(12) United States Patent
Hull (10) Patent No.: US 8,973,596 B2
(45) Date of Patent: Mar. 10, 2015

(54) APPLICATOR ASSEMBLY WITH INTEGRAL CHECK-VALVE

(71) Applicant: Confluent Surgical, Inc., Bedford, MA (US)

(72) Inventor: Les Hull, Attleboro, MA (US)

(73) Assignee: Confluent Surgical, Inc., Bedford, MA (US)

(*) Notice: Subject to any disclaimer, the term of this patent is extended or adjusted under 35 U.S.C. 154(b) by 39 days.

(21) Appl. No.: 13/914,674

(22) Filed: Jun. 11, 2013

(65) Prior Publication Data

US 2014/0014213 A1 Jan. 16, 2014

Related U.S. Application Data

(60) Provisional application No. 61/670,675, filed on Jul. 12, 2012.

(51) Int. Cl.
| | |
|---|---|
| *F17D 3/00* | (2006.01) |
| *F16K 15/02* | (2006.01) |
| *A61B 17/00* | (2006.01) |
| *B05B 7/04* | (2006.01) |
| *B05B 7/12* | (2006.01) |
| *B05B 12/08* | (2006.01) |
| *B01F 13/00* | (2006.01) |

(52) U.S. Cl.
CPC ......... *F16K 15/023* (2013.01); *A61B 17/00491* (2013.01); *B05B 7/0408* (2013.01); *A61B 2017/00495* (2013.01); *B05B 7/12* (2013.01); *B05B 12/088* (2013.01); *B01F 13/002* (2013.01); *B01F 2215/0039* (2013.01)
USPC .... 137/1; 137/533.19; 137/515.5; 137/515.7; 204/647

(58) Field of Classification Search
USPC ................ 137/515.5, 519, 533.19, 613, 2, 1, 137/15.18, 15.19, 533, 532, 515.7, 625.4; 604/247, 249
See application file for complete search history.

(56) References Cited

U.S. PATENT DOCUMENTS

| | | | |
|---|---|---|---|
| 274,308 A | | 3/1883 | George |
| 2,223,944 A | * | 12/1940 | Roy ............................. 137/517 |
| 3,593,713 A | | 7/1971 | Bogoff et al. |
| 3,844,290 A | | 10/1974 | Birch et al. |
| 4,300,572 A | | 11/1981 | Knighton |
| 4,325,366 A | | 4/1982 | Tabor |
| 4,354,492 A | * | 10/1982 | McPhee ........................ 604/247 |
| 4,416,273 A | | 11/1983 | Grimes |
| 4,447,230 A | | 5/1984 | Gula et al. |

(Continued)

*Primary Examiner* — Kevin Lee
*Assistant Examiner* — P. Macade Nichols
(74) *Attorney, Agent, or Firm* — Carter, DeLuca, Farrell & Schmidt LLP (57) ABSTRACT

A manifold for use with an applicator assembly is provided. The manifold includes a base having at least a first proximal extension and a distal extension. The at least first proximal extension includes an outer flange and an inner flange and defines a recess therebetween. The manifold further includes at least a first connection member securely affixed to the first proximal extension. The first connection member includes an annular flange configured to be received within the recess of the at least first proximal extension and the annular flange defines a proximal cavity. The manifold further includes at least a first seal member received within the proximal cavity between the first proximal extension and the first connection member. The seal member is configured to permit flow through the manifold in a first direction and obstruct flow through the manifold in a second direction.

6 Claims, 5 Drawing Sheets

(56) References Cited

U.S. PATENT DOCUMENTS

| | | |
|---|---|---|
| 4,449,693 A | 5/1984 | Gereg |
| 4,556,086 A | 12/1985 | Raines |
| 4,582,058 A | 4/1986 | Depel et al. |
| 4,657,530 A | 4/1987 | Buchwald et al. |
| 4,683,916 A | 8/1987 | Raines |
| 4,752,287 A | 6/1988 | Kurtz et al. |
| 4,776,369 A | 10/1988 | Lardner et al. |
| 4,883,456 A | 11/1989 | Holter |
| 4,946,448 A | 8/1990 | Richmond |
| 5,305,762 A | 4/1994 | Acorn et al. |
| 5,645,538 A | 7/1997 | Richmond |
| 5,738,095 A | 4/1998 | Persson |
| 5,992,462 A | 11/1999 | Atkinson et al. |
| 6,155,252 A | 12/2000 | Warters |
| 6,988,510 B2 | 1/2006 | Enerson |
| 7,025,784 B1 | 4/2006 | Blom et al. |
| 7,291,134 B2 | 11/2007 | Fitzgerald |
| 7,311,119 B2 | 12/2007 | Takehana et al. |
| 8,033,483 B2 * | 10/2011 | Fortier et al. ................ 239/399 |
| 8,051,856 B2 | 11/2011 | Bare et al. |
| 8,454,579 B2 | 6/2013 | Fangrow, Jr. |
| 8,523,826 B2 | 9/2013 | Layton, Jr. |
| 2010/0152680 A1 | 6/2010 | Mcmahon |
| 2011/0203590 A1 | 8/2011 | Unger et al. |
| 2011/0203691 A1 | 8/2011 | Gerlich et al. |

* cited by examiner

APPLICATOR ASSEMBLY WITH INTEGRAL CHECK-VALVE

CROSS-REFERENCE TO RELATED APPLICATIONS

This application claims the benefit of and priority to U.S. Provisional Patent Application No. 61/670,675, filed Jul. 12, 2012, the entire disclosure of which is incorporated by reference herein.

BACKGROUND

1. Technical Field

The present disclosure relates to assemblies for mixing and dispensing two or more components. More particularly, the present disclosure relates to an applicator assembly having a manifold with integrally formed check-valves.

2. Background of Related Art

Applicator assemblies for mixing and dispensing two or more components are known. Such assemblies typically include one or more check-valves to prevent flow of the components back into the source of the components. The check-valves are generally independently formed and are received between the sources of component and a manifold that directs the components into the mixing and dispensing portions of the assembly.

When using an applicator assembly with individually formed check-valves, the check-valves may become separated from the sources of component and/or the manifold. Further, because the check-valves and the applicator assemblies are typically provided by the supplier independently of each other, a ready supply of the various sized and types of check-valves is required to ensure that the proper check-valves for use with a given applicator assembly are readily available. Identifying and locating the proper check-valves increases the preparation time for a procedure and increases the possibilities for user error. In addition, the molding and manufacturing of separate manifolds and check-valves increases overall costs of the applicator assemblies.

Therefore, it would be beneficial to have an applicator assembly that includes a manifold with integrally formed check valves.

SUMMARY

A manifold for use with an applicator assembly is provided. The manifold includes a base having at least a first proximal extension and a distal extension. The at least first proximal extension includes an outer flange and an inner flange and defines a recess therebetween. The manifold further includes at least a first connection member securely affixed to the first proximal extension. The first connection member includes an annular flange configured to be received within the recess of the at least first proximal extension and the annular flange defines a proximal cavity. The manifold further includes at least a first seal member received within the proximal cavity between the first proximal extension and the first connection member. The seal member is configured to permit flow through the manifold in a first direction and obstruct flow through the manifold in a second direction.

In some embodiments, the first proximal extension may include a plurality of projections extending proximally from the inner flange. The plurality of projections may define channels therebetween. The first connection may include a peripheral flange fixedly connected with the outer flange of the at least first proximal extension. The peripheral flange and the outer flange may be ultrasonically welded together. Alternatively, the annular flange of the first connection member may be ultrasonic welded to the first proximal extension between the outer flange and the inner flange.

In other embodiments, the base includes a plurality of proximal extensions. The first connection member may be configured for operable connection with a source of component. The first seal member may be disc-shaped. The distal extension may be configured for operable connection to a mixing assembly. The base may define a first lumen extending from the at least first proximal extension to the distal extension.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Embodiments of the presently disclosed applicator assembly will now be described in detail with reference to the drawings in which like reference numerals designate identical or corresponding elements in each of the several views. Throughout this description, the term "proximal" will refer to the portion of the applicator assembly closest to the operator and the term "distal" will refer to the portion of the applicator assembly furthest from the operator.

Figure 1:
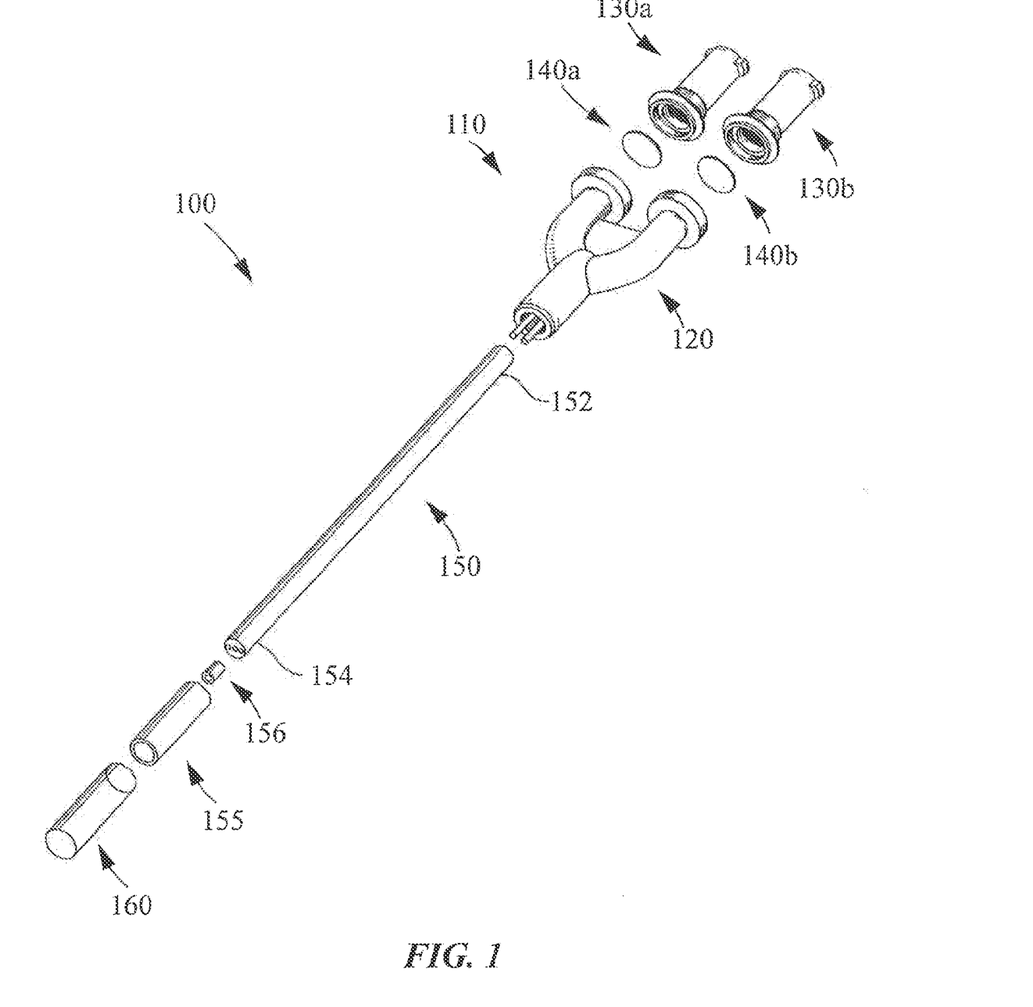
FIG. 1 is an exploded perspective view of an applicator assembly including a manifold according to an embodiment of the present disclosure.

Referring initially to FIG. 1, an applicator assembly according to an embodiment of the present disclosure is shown generally as applicator assembly 100. Applicator assembly 100 includes a manifold 110 having a base 120 and first and second connection members 130a, 130b extending proximally from base 110. Applicator assembly 100 further includes first and second seal member 140a, 140b received between base 110 and each of first and second connection members 130a, 130b, respectively. As will be discussed in further detail below, base 110 and first and second connection members 130a, 130b of manifold 110 and first and second seal members 140a, 140b, respectively, operate to form respective first and second check-valves 145a, 145b. An elongated body portion 150 extends distally from base 110. A mixing assembly 155, including an insert 156, operably engages a distal end of elongated body portion 150 and a sleeve 160 is configured to be received about mixing assembly 155 and the distal end 154 of elongated body portion 150.

Although the embodiments of the presently disclosed applicator assembly will be described as relates to applicator assembly 100, it is envisioned that the aspects of the present disclosure may be modified for use with applicator assemblies having alternative configurations. For example, applicator assembly 100 may be configured for use with alternative component supply assemblies and/or may include alternative mixing assemblies and/or alternative dispensing assemblies.

Figure 2:
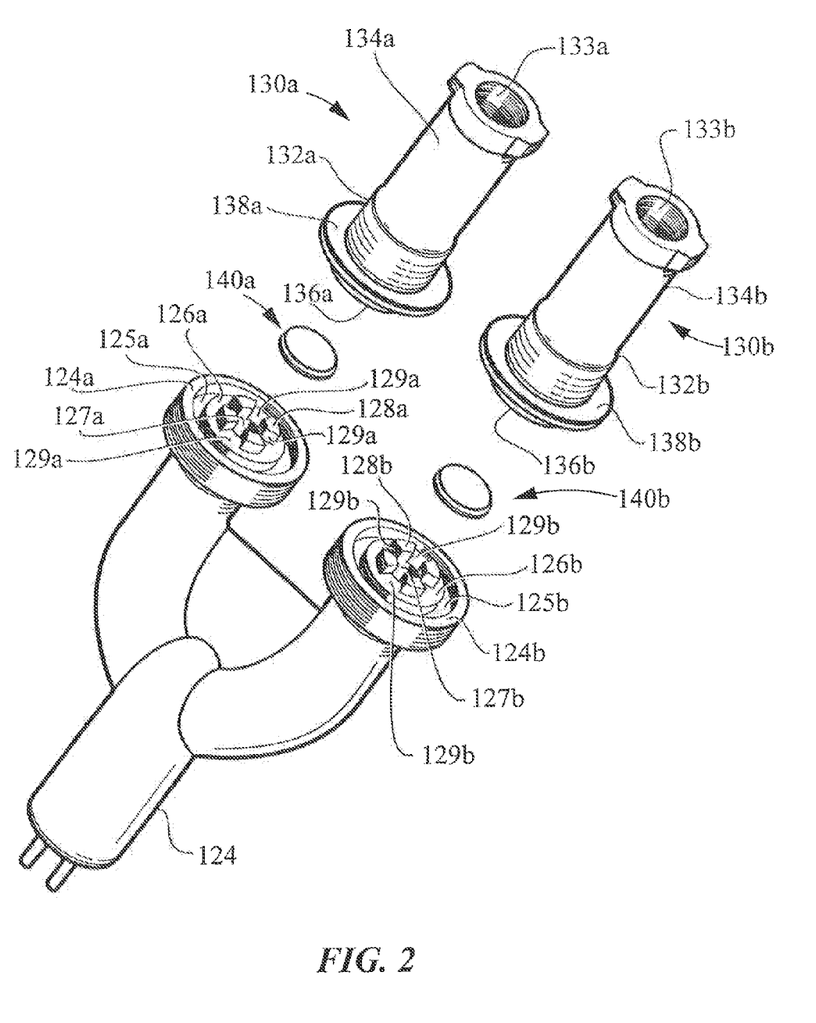
FIG. 2 is an enlarged exploded top perspective view of the manifold of the applicator assembly of FIG. 1.
Figure 3:
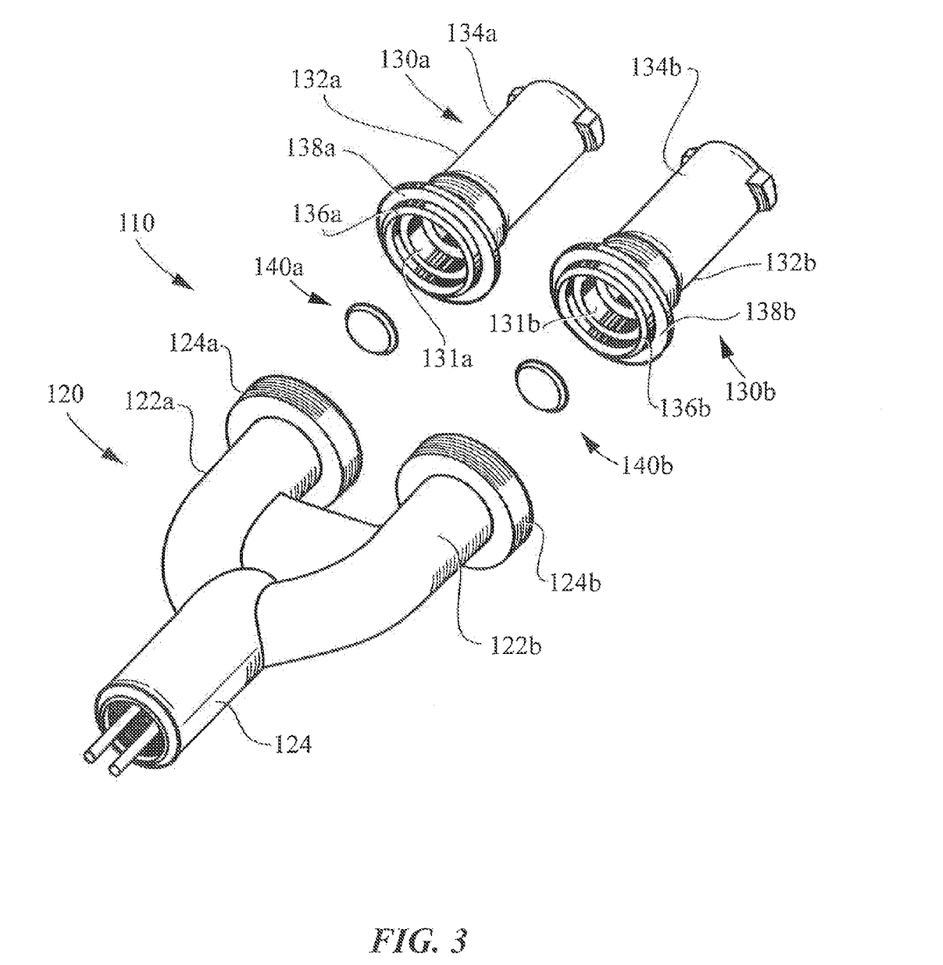
FIG. 3 is an enlarged exploded bottom perspective view of the manifold of FIG. 2.
Figure 4:
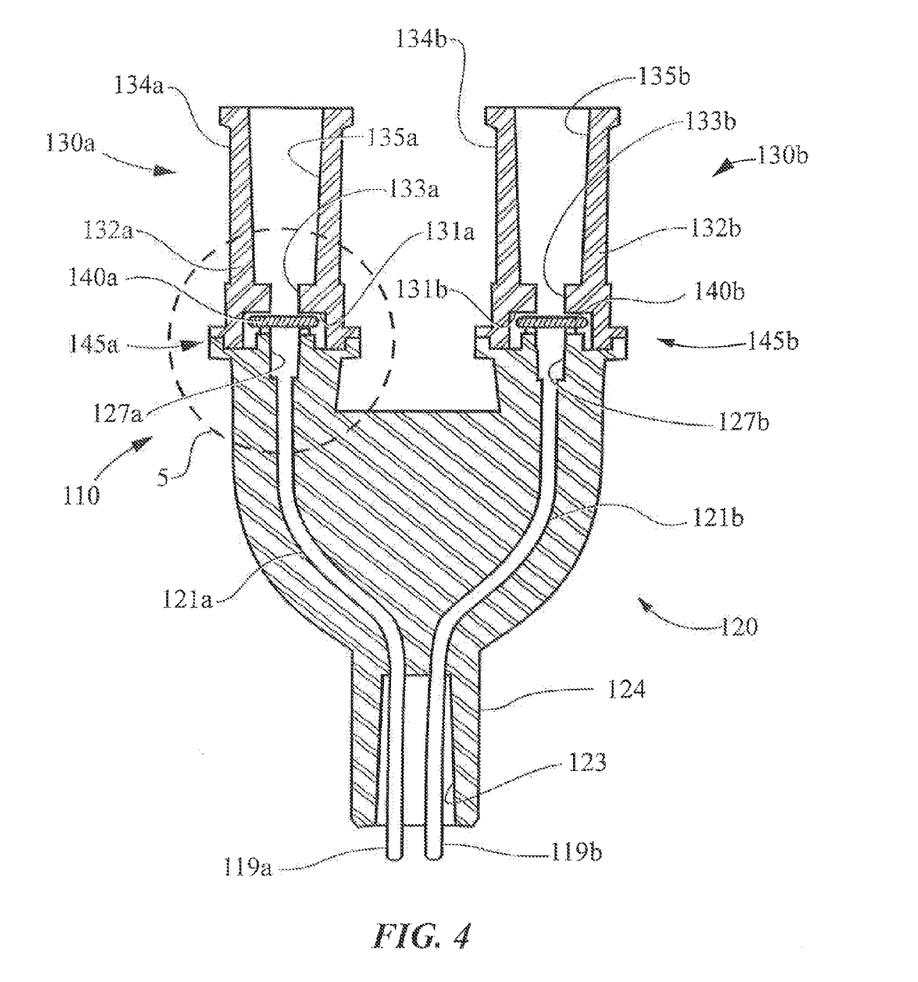
FIG. 4 is a cross-section side view of the manifold of FIGS. 2 and 3.

With reference now to FIGS. 2-4, manifold 110 of applicator assembly 100 includes substantially Y-shaped base 120 and first and second connection members 130a, 130b. Manifold 110 is configured to direct fluid from first and second sources of components (not shown) to elongated body portion 150. Although shown being configured to engage two sources of components, it is envisioned that the aspects of the present disclosure may be modified for use with applicator assemblies having only a single source of component or with applicator assemblies having multiple sources of components. If is further envisioned that manifold 110 may be configured for engagement with one or more different types of component sources.

With reference still to FIGS. 2-4, base 120 includes first and second proximal extension 122a, 122b and a distal extension 124. First and second proximal extensions 122a, 122b are each configured for fixed connection with first and second connection members 130a, 130b, respectively. Each of first and second proximal extensions 122a, 122b includes an outer flange 124a, 124b, respectively, and an inner flange 126a, 126b, respectively. Between each of outer flange 124a, 124b and inner flange 126a, 126b, respectively, each of respective first and second proximal extensions 122a, 122b defines an annular recess 125a, 125b, respectively. As will be discussed in further detail below, recesses 125a, 125b are configured to receive an annular flange 134a, 134b, respectively, of first and second connection members 130a, 130b, respectively. Inner flanges 126a, 126b each define an opening 127a, 127b, respectively. A plurality of projections 128a, 128b extend proximally from inner flange 126a, 126b and are radially spaced about respective openings 127a, 127b. Projections 128a, 128b define channels 129a, 129b, respectively, therebetween for directing component flowing from either of first and second connection members 130a, 130b, respectively, into respective openings 127a, 127b defined by inner flanges 126a, 126b, respectively. Although shown having four (4) projections 128a, 128b, each of first and second proximal extensions 122a, 122b may have fewer or more than four projections.

Still referring to FIGS. 2-4, distal extension 124 of base 120 is configured for operable connection with elongated body portion 150. In particular, distal extension 124 defines a cavity 123 for receiving a proximal end 152 of elongated body portion 150. Base 120 defines a pair of lumen 121a, 121b (FIG. 4) fluidly communicating openings 127a, 127b defined by inner flanges 126a, 126b, respectively, of first and second proximal extensions 122a, 122b, respectively, with cavity 123 defined by distal extension 124. In this manner, lumens 121a, 121b are configured to direct first and second components, respectively, from first and second proximal extensions 122a, 122b, respectively, through base 120 of manifold 110 to proximal end 152 of elongated body 150. In some embodiments, and as shown, first and second tubes 119a, 119b extend distally from distal extension 124 to form distal extensions from first and second lumen 121a, 121b, respectively. Each of first and second tubes 119a, 119b ensure proper alignment between manifold 110 and elongated body portion 150 during assembly. Although not shown, first and second tubes 119a, 119b may extend completely through base 120 of manifold 110 to form first and second lumens 121a, 121b, respectively, and to thereby fluidly communicate respective openings 127a, 127b with proximal end 152 of elongated body portion 150.

With continued reference to FIGS. 2-4, first and second connection members 130a, 130b include substantially tubular bodies having a distal end 132a, 132b, respectively, configured for fixed engagement with first and second proximal extensions 122a, 122b, respectively, of base 120 and a proximal end 134a, 134b configured for selective engagement with first and second sources of components (not shown), respectively. Distal ends 132a, 132b each include an annular flange 136a, 136b, respectively, and a peripheral flange 138a, 138b, respectively Annular flanges 136a, 136b are configured to be received within respective recesses 125a, 125b formed between outer and inner flanges 124a, 124b, 126a, 126b, respectively, of first and second proximal extensions 122a, 122b, respectively. Peripheral flanges 138a, 138b of respective first and second connection members 130a, 130b are configured to engage respective outer flanges 124a, 124b of first and second proximal extensions 122a, 122b, respectively. Peripheral flanges 138a, 138b and outer flanges 124a, 124b, respectively, may be secured to one another by heat staking, adhesives, mechanical fasteners or any other suitable method. In one embodiment, peripheral flanges 138a, 138b and outer flanges 124a, 124b are ultrasonically welded together. In an alternative embodiment, annular flanges 136a, 136b and annular recesses 125a, 125b are ultrasonically welded together.

Annular flanges 136a, 136b and peripheral flanges 138a, 138b of respective first and second connection members 130a, 130b and outer flanges 124a, 124b of respective first and second proximal extensions 122a, 122b are configured to form a fluid tight seal between first and second proximal connection members 130a, 130b and first and second proximal extensions 122a, 122b, respectively, of base 120. Alternatively, or in addition, a sealant (not shown) may be received between first and second connection members 130a, 130b and first and second proximal extensions 122a, 122b, respectively, to create a fluid tight seal therebetween.

With continued reference to FIGS. 2-4, proximal ends 134a, 134b of first and second connection members 130a, 130b, respectively, are configured for selective engagement with first and second sources of component (not shown), respectively. As shown, each of proximal ends 134a, 134b is configured for a luer-type connection with a syringe or other suitable source of component. Alternatively, proximal ends 134a, 134b may be configured for threaded connection, snap-fit engagement, bayonet coupling and/or any other suitable connection with first and second sources of components. As noted above, it is envisioned that each of proximal ends 134a, 134b may be configured for selective engagement with a different type of component source.

With particular reference now to FIG. 4, first and second connection members 130a, 130b each define a distal cavity 131a, 131b, respectively, a proximal cavity 133a, 133b, respectively, and a passageway 135a, 135b, respectively, therebetween. Distal cavities 131a, 131b are defined by annular flanges 136a, 136b, respectively, and are configured to operably receive projections 128a, 128b, respectively, formed on respective inner flanges 126a, 126b of first and second proximal extensions 122a, 122b, respectively. As will be discussed in further detail below, distal cavities 131a, 131b are of a depth such that, when first and second connection members 130a, 130b are connected to respective first and second proximal extensions 122a, 122b with first and second seal member 140a, 140b, respectively, received therebetween, there is sufficient space between respective first and second seal members 140a, 140b and passageway 135a, 135b, respectively, of each of first and second connection members 130a, 130b, respectively, to permit fluid to flow from passageways 135a, 135b, around first and second seal members 140a, 140b, respectively, and through respective channels 129a, 129b into openings 127a, 127b, respectively, of first and second proximal extensions 122a, 122b, respectively. In this manner, and as noted above, each of first and second proximal extensions 122a, 122b, first and second connection members 130a, 130b and first and second seal members 140a, 140b, respectively, operate as first and second check-valves 145a, 145b, respectively, to prevent component from flowing back into the sources of component.

With reference back to FIGS. 2-4, first and second seal members 140a, 140b each define a solid, resilient disc having a rounded or beveled edge. First and second seal members 140a, 140b may be formed of plastic, silicone, polymer or other suitable material. First and second seal members 140a, 140b are sized to be received within cavity 131a, 131b, respectively, of first and second connection members 130a, 130b, respectively, between first and second projections 128a, 128b, respectively, and first and second passageway 135a, 135b, respectively, defined by first and second connection members 130a, 130b, respectively. First and second seal members 140a, 140b each have a diameter that is sufficiently large to cover openings 127a, 127b, respectively, of first and second proximal extensions 122a, 122b, respectively, and first and second passageway 135a, 135b, respectively, of first and second connection members 130a, 130b. The diameters of each of first and second seal members 140a, 140b are smaller then the diameter of distal cavities 131a, 131b, respectively, such that the first and second components are permitted to flow from respective first and second passageways 135a, 135b, around each of first and second seal members 140a, 140b and through respective channels 129a, 129b formed between first and second projections 128a, 128b, respectively, and into respective openings 127a, 127b. In some embodiment, the diameters of first and second seal members 140a, 140b are such that first and second seal members 140a, 140b do not extend outwardly of respective first and second projections 128a, 128b.

Distally of manifold 110 the structure and function of applicator assembly 100 is substantially similar to traditional spray applicator assembly. For a detailed discussion of applicator assembly 100 distally of manifold 110, please refer to commonly owned U.S. Pat. No. 8,033,483, the content of which is incorporated herein by reference in its entirety.

Figure 5A:
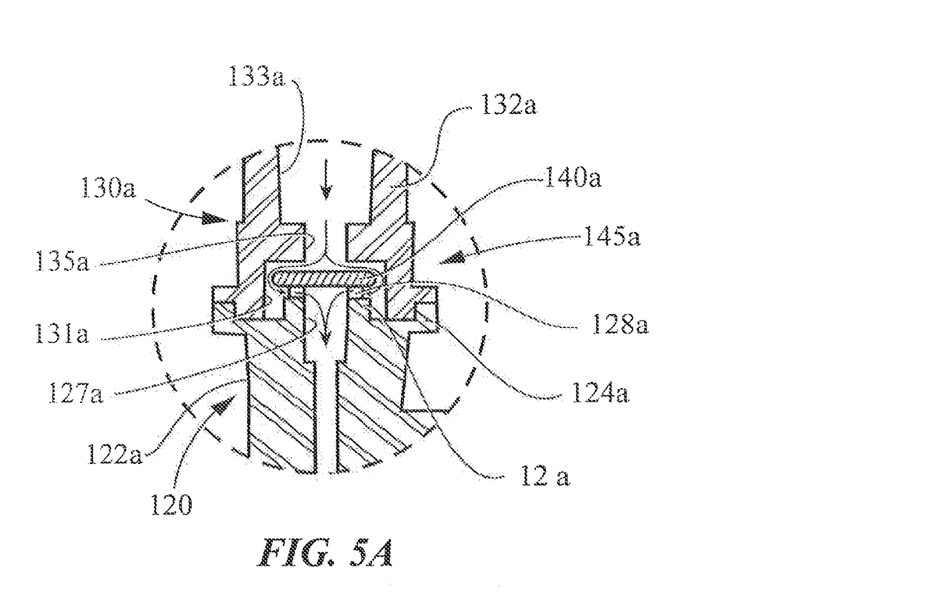
FIG. 5A is an enlarged view of Section 5 of FIG. 4 showing the check-valve of manifold of FIG. 4 in an open configuration.

The operation of manifold 110 and first and second check-valves 145a, 145b, in particular, will now be described with reference to FIGS. 5A and 5B. Turning initially to FIG. 5A, while applying a mixture of a first and second component using applicator assembly 100, the first and second components flow from first and second sources of component, respectively, into respective first and second proximal cavities 133a, 133b of first and second connection members 130a, 130b, respectively, and through respective first and second passageway 135a, 135b of first and second connection members 130a, 130b, respectively. The first and second components then flow over and around first and second seal members 140a, 140b, respectively, through respective channels 129a, 129b formed between first and second projections 128a, 128b, respectively, and into respective first and second openings 127a, 127b. In this manner, the first and second components are provided to proximal end 152 of elongated body portion 150 and, ultimately, to mixing assembly 155, in a controlled manner.

Figure 5B:
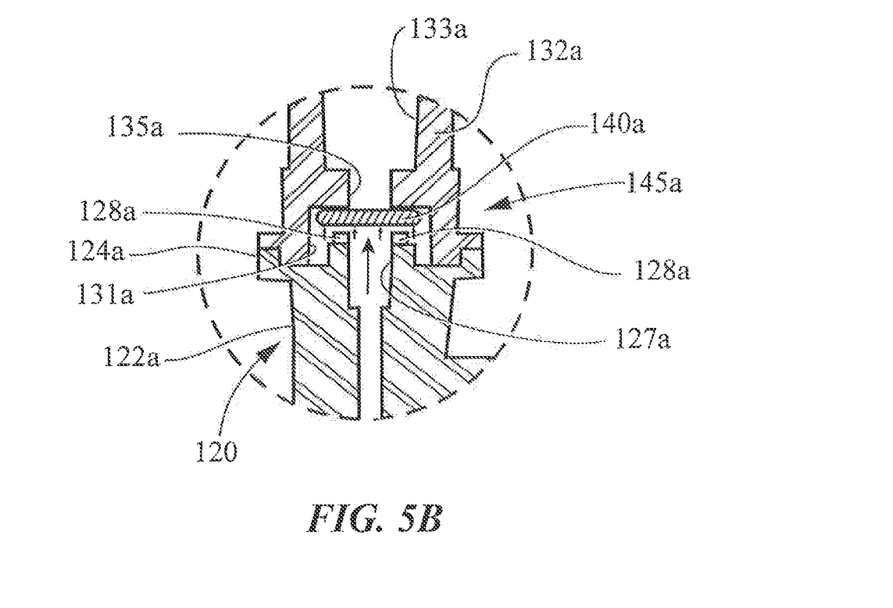
FIG. 5B is the enlarged view of Section 5 of FIG. 4, showing the check-valve in a closed configuration

Turning now to FIG. 5B, in the event that either or both of the first and second components flows in a reverse direction through lumen 121a, 121b, respectively, of manifold 110 and into respective openings 127a, 127b of first and second proximal extensions 122a, 122b, respectively, the first and/or second component will flow against respective first and second seal members 140a, 140b. The back-flow of the first and/or second components against first and/or second seal members 140a, 140b, respectively, causes proximal displacement of respective first and second seal members 140a, 140b within cavities 131a, 131b, respectively. The force exerted by the flow of the first and second components against each of first and second seal members 140a, 140b causes each of first and second seal members 140a, 140b to engage first and second connection members 130a, 130b, respectively, about first and second passageways 135a, 135b, respectively, of first and second connection members 130a, 130b, respectively, thereby obstructing flow through first and second passageways 135a, 135b, respectively. In this manner, the first and second components are prevented, or checked, from flowing back into first and second connection members 130a, 130b and, ultimately, back into the first and second sources of component.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method of assembling an applicator assembly, the method comprising:
   providing a base including first and second proximal extensions and a distal extension, each of the first and second proximal extensions including an outer flange and an inner flange and defining a recess between the outer flange and the inner flange;
   providing first and second connection members each including an annular flange and a peripheral flange;
   receiving a first seal member between the first proximal extension of the base and the first connection member and a second seal member between the second proximal extension of the base and the second connection member;
   receiving the annular flanges of the first and second connection members within the recesses of the first and second proximal extensions;
   creating a fluid tight seal between the first and second proximal extensions of the base and the first and second connection members by fixedly connecting the peripheral flanges of the first and second connection members to the outer flanges of the first and second proximal extensions; and
   operably engaging a mixing assembly with the distal extension of the base.

2. The method of claim 1, wherein creating a fluid tight seal between the first and second proximal extensions of the base and the first and second connection members by fixedly connecting the peripheral flanges of the first and second connection members to the outer flanges of the first and second proximal extensions includes heat staking, ultrasonically welding, or adhering the peripheral flanges to the outer flanges.

3. The method of claim 1, wherein operably engaging the mixing assembly with the distal extension of the base includes engaging a proximal end of an elongated body portion with the distal extension and engaging the mixing assembly with a distal end of the elongated body.

4. The method of claim 3, wherein operably engaging the mixing assembly with the distal extension further includes receiving a sleeve about the mixing assembly and the distal end of the elongated body portion.

5. The method of claim 1, further including connecting a first source of a first component to the first connection member and a second source of a second component to the second connection member.

6. The method of claim 1, wherein the first seal member and the second seal member are configured to permit flow through the base in a first direction and obstruct flow through the base in a second direction.

* * * * *